(12) United States Patent
Nawaz et al.

(10) Patent No.: US 10,035,120 B2
(45) Date of Patent: Jul. 31, 2018

(54) REACTORS FOR SEPARATING WAX PRODUCTS FROM LIGHTWEIGHT GASEOUS PRODUCTS OF A REACTION

(71) Applicant: SABIC Global Technologies B.V., Bergen op Zoom (NL)

(72) Inventors: Zeeshan Nawaz, Riyadh (SA); Shahzada Khuram, Riyadh (SA); Khalid Karim, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/521,357

(22) PCT Filed: Oct. 29, 2015

(86) PCT No.: PCT/IB2015/058357
§ 371 (c)(1),
(2) Date: Apr. 24, 2017

(87) PCT Pub. No.: WO2016/067244
PCT Pub. Date: May 6, 2016

(65) Prior Publication Data
US 2017/0312722 A1  Nov. 2, 2017

Related U.S. Application Data

(60) Provisional application No. 62/073,331, filed on Oct. 31, 2014.

(51) Int. Cl.
*B01J 8/06* (2006.01)
*C10G 2/00* (2006.01)
*C07C 1/04* (2006.01)

(52) U.S. Cl.
CPC .............. *B01J 8/065* (2013.01); *B01J 8/067* (2013.01); *C07C 1/041* (2013.01); *C10G 2/341* (2013.01);
(Continued)

(58) Field of Classification Search
CPC ...... B01J 8/065; B01J 8/067; B01J 2208/065; B01J 2208/00212; C10G 2/341; C10G 2400/20; C10G 2400/22; C07C 1/041
See application file for complete search history.

(56) References Cited

U.S. PATENT DOCUMENTS 5,405,586 A   4/1995  Koves
6,068,760 A   5/2000  Benham et al.
(Continued)

FOREIGN PATENT DOCUMENTS

CA    2274579 C    6/1998
CN    102698662 A  10/2012
(Continued)

OTHER PUBLICATIONS

Van der Laan et al. "Kinetics and Selectivity of the Fischer-Tropsch Synthesis: A Literature Review" in Catal. Rev.-Sci. Eng., 41, 1999, p. 255 (Abstract).
(Continued)

*Primary Examiner* — Jafar Parsa
(74) *Attorney, Agent, or Firm* — Ballard Spahr LLP

(57) ABSTRACT

A reactor for hydrocarbon production that separates wax reaction products from lightweight gaseous reaction products. The reactor has a housing, a catalyst bed, a product recovery zone, and a stripping zone. The catalyst bed can be provided in multi-tubular and other fixed bed configurations. The stripping zone receives light-weight gas reaction products from the product recovery zone, while a gas outlet of the housing receives non-lightweight gaseous hydrocarbon reaction products from the product recovery zone. A wax outlet of the housing receives wax products from the product recovery zone.

20 Claims, 6 Drawing Sheets

(52) U.S. Cl.
CPC ........... *B01J 2208/00212* (2013.01); *B01J 2208/065* (2013.01); *C10G 2400/20* (2013.01); *C10G 2400/22* (2013.01)

(56) References Cited

U.S. PATENT DOCUMENTS

| | | |
|---|---|---|
| 6,590,002 B2 | 7/2003 | Wittenbrink et al. |
| 6,846,848 B2 | 1/2005 | Wittenbrink et al. |
| 6,958,135 B1 | 10/2005 | Filippi et al. |
| 8,506,895 B2 | 8/2013 | Wang et al. |
| 2004/0102530 A1 | 5/2004 | Borsa et al. |

FOREIGN PATENT DOCUMENTS

| | | |
|---|---|---|
| CN | 202725143 U | 2/2013 |
| EP | 0534195 A1 | 3/1993 |
| EP | 1153653 A1 | 11/2001 |
| EP | 1221339 A1 | 7/2002 |
| EP | 1306126 A1 | 5/2003 |
| EP | 1216750 B1 | 8/2006 |
| EP | 1788335 A1 | 5/2007 |
| GC | 30278 | 10/2015 |
| GC | 30283 | 10/2015 |
| IN | 201717013920 | 10/2015 |
| IN | 201717013921 | 10/2015 |
| JP | PCT/IB2015/058357 | 10/2015 |
| JP | PCT/IB2015/058359 | 10/2015 |
| WO | WO-01/053430 A1 | 7/2001 |
| WO | WO-2003/006404 A1 | 1/2003 |
| WO | WO-2005/063616 A1 | 7/2005 |
| WO | PBT/IB2015/058357 | 10/2015 |
| WO | PCT/IB2015/058357 | 10/2015 |
| WO | PCT/IB2015/058359 | 10/2015 |
| WO | WO-2016/067244 A1 | 5/2016 |
| WO | WO-2016/067245 A1 | 5/2016 |

OTHER PUBLICATIONS

International Search Report and Written Opinion dated Mar. 4, 2016 by the International Searching Authority for International Application No. PCT/IB2015/058359, which was filed on Oct. 29, 2015 and published as WO2016/067245 on May 6, 2016 (Applicant—Sabic Global Technologies B.V.) (17 pages).

International Search Report and Written Opinion dated Apr. 1, 2016 by the International Searching Authority for International Application No. PCT/IB2015/058357, which was filed on Oct. 29, 2015 and published as WO2016/067244 on May 6, 2016 (Applicant—Sabic Global Technologies B.V.) (11 pages).

U.S. Appl. No. 62/072,778, filed Oct. 30, 2014, Zeeshan Nawaz.
U.S. Appl. No. 15/521,354, filed Apr. 24, 2017, Zeeshan Nawaz.
U.S. Appl. No. 62/073,331, filed Oct. 31, 2014, Zeeshan Nawaz.

REACTORS FOR SEPARATING WAX PRODUCTS FROM LIGHTWEIGHT GASEOUS PRODUCTS OF A REACTION

CROSS-REFERENCE TO RELATED APPLICATIONS

This is a U.S. National Phase Application of International Application No. PCT/IB2015/058357, filed Oct. 29, 2015, which claims the benefit of U.S. Provisional Application No. 62/073,331, filed Oct. 31, 2014, which are both incorporated herein by reference in their entirety.

FIELD

This invention relates to reactors for separating wax or higher-weight products (heavies) from lower-weight gaseous products of a chemical reaction and, more particularly, to reactors for separating wax or higher-weight products from lower weight gaseous products of a syngas conversion reaction.

BACKGROUND

Syngas conversion reactions and other reactions that produce lower-weight reaction products, such as lower olefins and paraffins, can produce hydrocarbon wax and other higher-weight reaction products. Such reactions require robust control over reaction and heat constraints, and the wax formation rate can be lower than in reactions that produce higher-weight reaction products. Typically, after a reaction is completed, all reaction products are transferred from the reactor to a separate apparatus, wherein a wax separation process is performed. Such a wax separation process significantly increases the capital and operation costs associated with the overall reaction process. There is a need in the art for reactors that permit separation and removal of wax from within the reactor to reduce the capital and operation costs associated with chemical reactions, particularly syngas conversion reactions and other reactions that produce lower-weight reaction products.

SUMMARY

Described herein, in one aspect, is a reactor for separating wax products from lightweight gaseous products of a chemical reaction. The reactor can have a housing, a catalyst bed, a product recovery zone, a stripping zone, and a scraper. The housing can define a gas feed inlet, a gas outlet, and a wax product outlet. The housing can have a longitudinal axis, an upper end, and an opposed lower end. The gas feed inlet can be positioned proximate the upper end of the housing. The catalyst bed can be positioned within the housing in fluid communication with the gas feed inlet. The catalyst bed can be configured to receive at least one catalyst. The product recovery zone can be positioned within the housing in fluid communication with the catalyst bed. The stripping zone can be positioned in fluid communication with the product recovery zone and the gas outlet. The stripping zone can extend upwardly from the product recovery zone relative to the longitudinal axis of the housing. The stripping zone can be configured to receive light-weight gaseous products from the product recovery zone. The scraper can be positioned within the product recovery zone. The scraper can be configured to separate wax products from non-wax products of the at least one reaction product. The gas outlet can be configured to receive lightweight gas reaction products from the stripping zone, and the wax product outlet can be configured to receive wax products from the product recovery zone.

In another aspect, described herein is a reactor for separating wax products from lightweight gaseous products of a chemical reaction. The reactor can have a housing, a plurality of tubes, a plurality of coolant plates, a product recovery zone, and a stripping zone. The housing can define a gas feed inlet, a gas outlet, and a wax product outlet. The housing can have a longitudinal axis, an upper end, and an opposed lower end. The gas feed inlet can be positioned proximate the upper end of the housing. The plurality of tubes can be positioned in fluid communication with the gas feed inlet and configured to receive at least one catalyst. The plurality of coolant plates can be circumferentially spaced within the housing. Adjacent coolant plates of the plurality of coolant plates can cooperate with interior surfaces of the reactor to circumferentially surround at least a portion of at least one tube of the plurality of tubes. Each coolant plate defines at least one channel configured to receive at least one coolant. The product recovery zone can be positioned within the housing in fluid communication with the plurality of tubes. The product recovery zone can be positioned below the plurality of tubes relative to the longitudinal axis of the housing and be configured to receive at least one reaction product. The stripping zone can be positioned in fluid communication with the product recovery zone and the gas outlet. The stripping zone can extend upwardly from the product recovery zone relative to the longitudinal axis of the housing. The stripping zone can be configured to receive light-weight gaseous products from the product recovery zone. The gas outlet can be configured to receive non-lightweight gas reaction products from the stripping zone, and the wax product outlet can be configured to receive wax products from the product recovery zone.

Methods of using the described reactors to perform a chemical reaction are also disclosed. In exemplary aspects, the described reactors can be used to perform a syngas conversion reaction.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein:

FIG. 1 is an isolated perspective view of an exemplary arrangement for the coolant feed, gas stripping zone, and product recovery zone of a reactor as disclosed herein. As shown, the reactor comprises coolant plates that permit axial flow of coolant within the reactor in a first direction. As coolant exits the plates, it enters a coolant outlet, which permits radial flow of the coolant (for example, flow that is substantially perpendicular to the longitudinal axis of the reactor) and then axial flow of the coolant in a second direction opposite the first direction. Coolant within the coolant outlet can then be recirculated as further disclosed herein.

FIG. 2 is a top cross-sectional view of an exemplary reactor as disclosed herein. As shown, the reactor can have a plurality of plates positioned within a catalyst bed, and a center portion of the reactor can define a stripping area that permits stripping of light-weight gaseous products away from wax products or heavies. The lighter-weight gaseous products can be collected from the stripping zone through a gas outlet defined in a top portion of the reactor.

Figure 1:
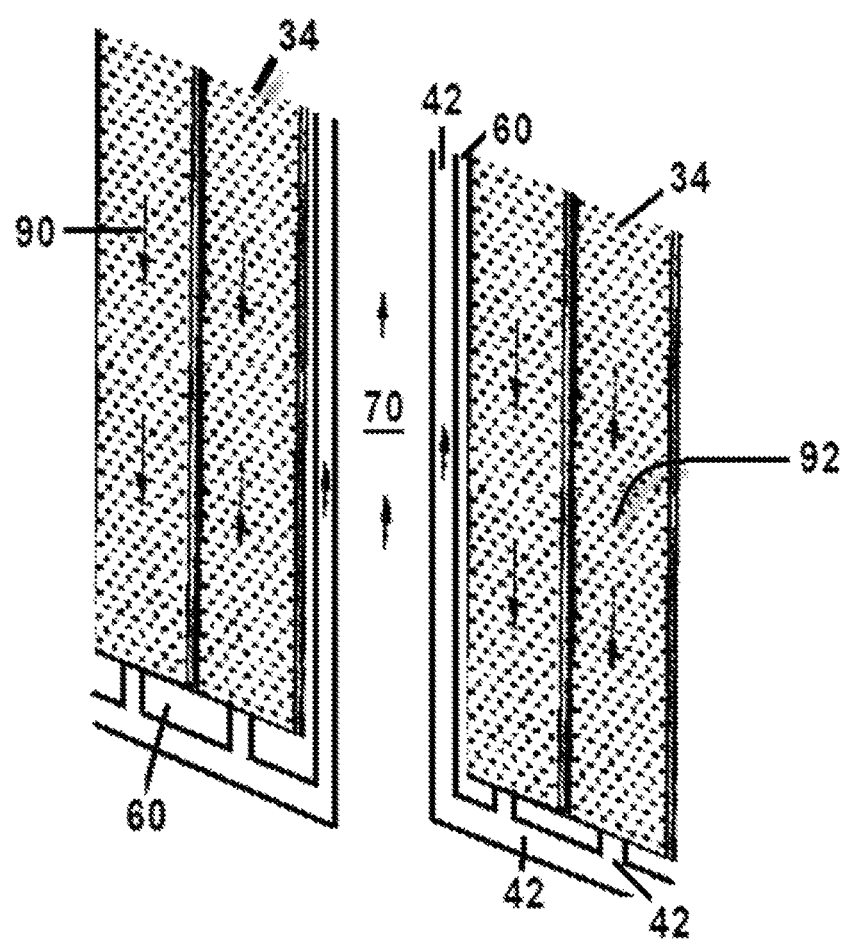
Figure 2:
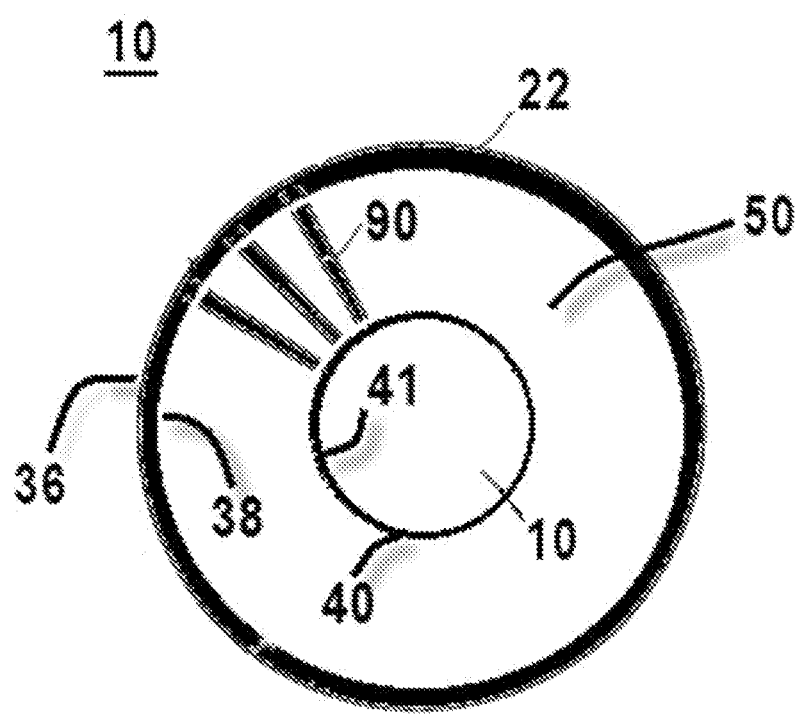
Figure 3:
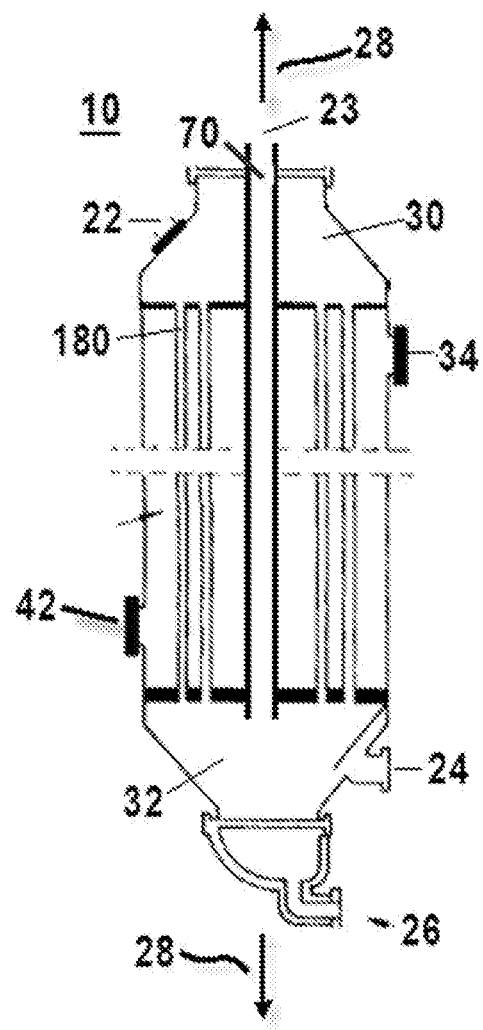
FIG. 3 is a side cross-sectional view of an exemplary reactor as disclosed herein. As shown, the reactor has a plurality of tubes, a stripping zone, and a wax product collection outlet in communication with a product collection area.
Figure 4:
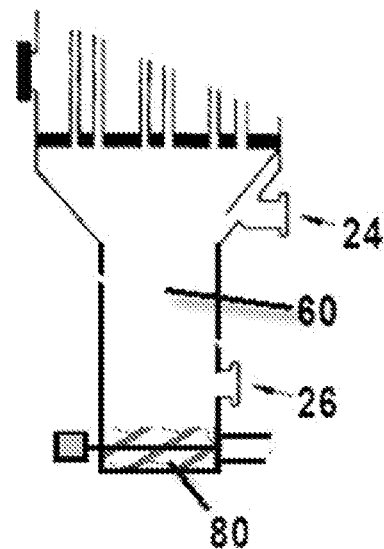
FIG. 4 is an isolated side cross-sectional view of the product collection area of an exemplary reactor as disclosed herein. As shown, the product collection area can have a separating zone with respective outlets for gas and wax reaction products and a scraper to help remove the wax reaction products from the product collection area.
Figure 5:
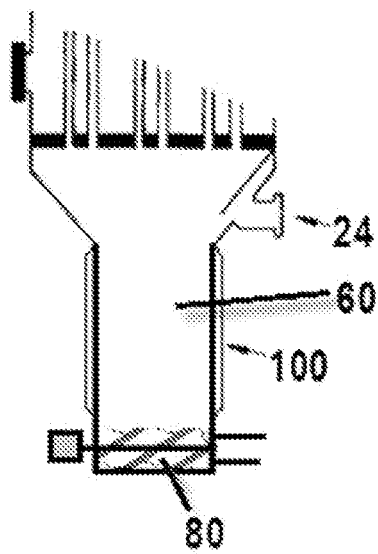

FIG. 5 is an isolated side cross-sectional view of the product collection area of an exemplary reactor as disclosed herein. As shown, the product collection area can have a separating zone with respective outlets for gas and wax reaction products and a scraper to help remove the wax reaction products from the product collection area. Additionally, the reactor has a cooling jacket that surrounds at least a portion of the product collection area and is configured to help promote separation of the wax reaction products from the lightweight reaction products.

Figure 6:
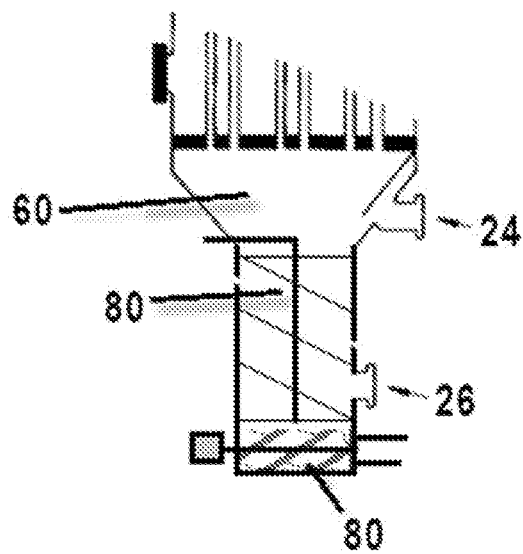

FIG. 6 is an isolated side cross-sectional view of the product collection area of an exemplary reactor as disclosed herein. As shown, the product collection area can have a separating zone with respective outlets for gas and wax reaction products and a first scraper to help remove the wax reaction products from the product collection area. Additionally, the reactor can have a second scraper positioned within the product collection area to separate the wax reaction products from the gas reaction products.

Figure 7:
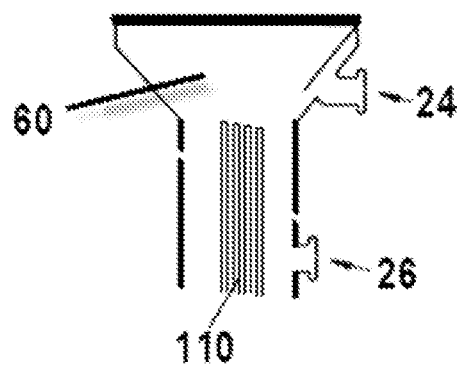

FIG. 7 is an isolated side cross-sectional view of the product collection area of an exemplary reactor as disclosed herein. As shown, the product collection area can have a separating zone with respective outlets for gas and wax reaction products and a heat exchanger/evaporator positioned within the product collection area to separate the wax reaction products from the gas reaction products.

Figure 8:
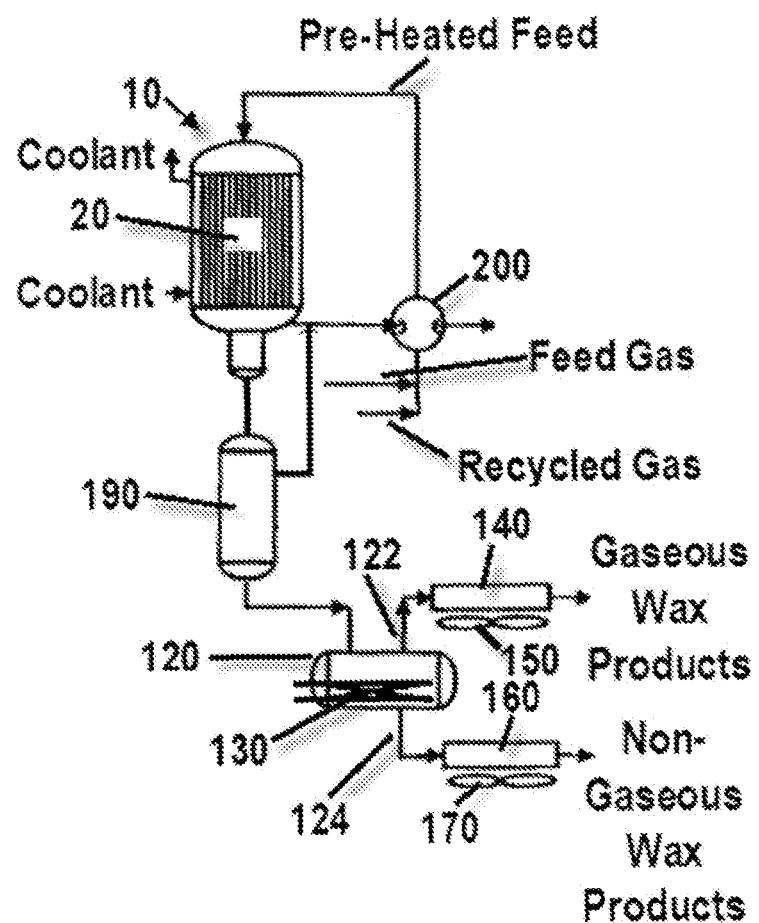

FIG. 8 is a schematic diagram depicting an exemplary system for separating and treating wax reaction products as disclosed herein.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

All publications mentioned herein are incorporated herein by reference to disclose and describe the methods and/or materials in connection with which the publications are cited.

As used throughout, the singular forms "a," "an" and "the" include plural referents unless the context clearly dictates otherwise. Thus, for example, reference to "a wax outlet" can include two or more such wax outlets unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, the term "lightweight" or "lower-weight" refers to gaseous reaction products that are substantially free of hydrocarbon reaction products that can be classified as wax and/or heavies as are conventionally known in the art. For example, in exemplary aspects, it is contemplated that hydrocarbons of C18 and lower can be considered as "lightweight" gaseous reaction products, whereas hydrocarbon reaction products of C19 and greater are referred to herein as "wax products" or "wax reaction products." As further disclosed herein, it is contemplated that "wax products" can comprise at least one of wax, heavies, and non-lightweight gaseous hydrocarbons (gaseous wax products). Thus, it is understood that the "wax products" disclosed herein can comprise non-wax components, such as, for example, and without limitation, heavies and non-lightweight gaseous hydrocarbons. As further disclosed herein, it is contemplated that the "lightweight" gaseous reaction products can be a mixture of individual components. Similarly, it is contemplated that the wax reaction products can be a mixture of individual components. The wax and heavies within the wax products are generally referred to herein as "non-gaseous wax products." As used herein, the term "heavies" refers to non-gaseous wax products that are not conventionally referred to as wax in the art.

The Reactor

Described herein with reference to FIGS. 1-8 is a reactor 10 for separating wax products from lightweight gaseous products of a chemical reaction. In exemplary aspects, the reactor can comprise a housing 20, a catalyst bed 50, a product recovery zone 60, and a stripping zone 70. Optionally, in these aspects, the reactor 10 can further comprise a scraper 80.

In one aspect, and with reference to FIGS. 2-7, the housing 10 can define a gas feed inlet 22, a first gas outlet 23, and a wax product outlet 26. In another aspect, the housing 20 can have a longitudinal axis 28, an upper end 30, and an opposed lower end 32. In this aspect, it is contemplated that the gas feed inlet 22 can be positioned proximate the upper end 30 of the housing 20. It is contemplated that the upper end 30 of the housing 20 can define a homogenization zone within the reactor 10. However, it is contemplated that the gas feed inlet 22 can be defined in any portion of the housing 20 that permits gas flow as disclosed herein, including, for example and without limitation, a side wall of the housing. In a further aspect, the housing 20 can define at least one coolant inlet 34 and at least one coolant outlet 42. In this aspect, the at least one coolant inlet 34 can be configured to receive at least one coolant to permit circulation of the at least one coolant within the housing 20. Optionally, the at least one coolant outlet 42 can be spaced from the at least one coolant inlet 34 relative to the longitudinal axis 28 of the housing 20. It is contemplated that the flow of coolant from the coolant inlet 34 to the coolant outlet 42 can be substantially parallel to the longitudinal axis 28 of the housing 20, including in an upward or a downward direction. It is further contemplated that the direction of coolant flow can be selectively adjusted as needed, with the coolant inlet 34 optionally serving as an outlet and the coolant outlet 42 optionally serving as an inlet.

In an additional aspect, the catalyst bed 50 can be positioned within the housing 20 in fluid communication with the gas feed inlet 22. In this aspect, the gas feed inlet 22 can be configured to receive at least one gas, and the catalyst bed 50 can be configured to receive at least one catalyst, thereby permitting reaction between the at least one gas and the at least one catalyst.

In a further aspect, the product recovery zone 60 can be positioned within the housing 20 in fluid communication with the catalyst bed 50. In this aspect, the product recovery zone 60 can be configured to receive at least one reaction product following reaction between the at least one gas and the at least one catalyst. In exemplary aspects, the at least one gas can optionally be configured for axial flow relative to the longitudinal axis 22 of the housing 20. In these aspects, it is contemplated that the product recovery zone 60 can be positioned below the catalyst bed 50 relative to the longitudinal axis 28 of the housing 20. In other exemplary aspects, the at least one gas can optionally be configured for radial flow within the catalyst bed 50 substantially perpendicular to the longitudinal axis 22 of the housing 20 (i.e., in a radial flow reactor). In these aspects, it is contemplated that the product recovery zone 60 can be positioned above or below the catalyst bed 50. It is further contemplated that the product recovery zone 60 can optionally be positioned radially inwardly or outwardly of the catalyst bed 50.

In another aspect, the stripping zone 70 can be positioned in fluid communication with the product recovery zone 60 and the first gas outlet 23. Optionally, the stripping zone 70 can extend upwardly from the product recovery zone relative to the longitudinal axis 28 of the housing 20. It is contemplated that the stripping zone 70 can be configured to receive light-weight gas reaction products from the product recovery zone 60.

In operation, the first gas outlet 23 of the housing 20 can be configured to receive lightweight gas reaction products from the stripping zone 70, and the wax product outlet 26 of the housing can be configured to receive wax products from the product recovery zone 60. In exemplary aspects, the housing can further define a second gas outlet 24 proximate the lower end 32 of the housing and in fluid communication with the product recovery zone 60. In these aspects, the second gas outlet 24 can be configured to receive non-lightweight gaseous products from the product recovery zone 60. Optionally, the second gas outlet 24 can optionally be positioned in fluid communication with a gas line 25 that is configured to permit heating of the gas material to be provided to the gas inlet 22. Optionally, in these aspects, it is contemplated that the gas line can be positioned in communication with a gas-gas exchanger 200 that provides heating of gas before it is provided to the gas inlet 22. Optionally, in exemplary aspects, at least a portion of the gas provided to the gas inlet 22 can be recycled and reused.

Optionally, in exemplary aspects, a scraper 80 can be positioned within the product recovery zone 60. In these aspects, the scraper 80 can be configured to separate wax products from interior surfaces of the housing 20. Optionally, the scraper 80 can be a mechanical scraper as is known in the art. In exemplary aspects, the scraper 80 can be motorized. In other exemplary aspects, it is contemplated that a plurality of scrapers can be provided within the product recovery zone 60. In other exemplary aspects, it is contemplated that at least one baffle can be positioned within the product recovery zone 60 to help separate wax products from lightweight gaseous products.

In further optional aspects, the reactor 10 can further comprise a plurality of coolant plates 90. In these aspects, the plurality of coolant plates 90 can be circumferentially spaced within the catalyst bed 50. In exemplary, optional aspects, the plurality of coolant plates 90 can be substantially evenly circumferentially spaced within the housing 20. In another aspect, each coolant plate 90 of the plurality of coolant plates can define at least one channel 92 configured to receive at least one coolant. In this aspect, it is contemplated that the channels 92 of the plurality of coolant plates 90 can be positioned in fluid communication with the coolant inlet 34. Optionally, it is further contemplated that the channels 92 of the plurality of coolant plates 90 can be positioned in fluid communication with the coolant outlet 42. In exemplary aspects, the channels 92 of the coolant plates 90 can be substantially parallel to the longitudinal axis 28 of the housing 20. Thus, in these aspects, the coolant plates 90 can be configured to permit coolant flow in a direction substantially parallel to the longitudinal axis 28 of the housing 20. Alternatively, in other aspects, it is contemplated that the channels 92 of the coolant plates 90 can be substantially perpendicular to the longitudinal axis 28 of the housing 20. Thus, in these aspects, the coolant plates can be configured to permit coolant flow in a direction substantially perpendicular to the longitudinal axis 28 of the housing 20.

Optionally, in exemplary aspects, the plurality of coolant plates 90 can be secured within the housing 20 before the at least one catalyst is positioned within the catalyst bed 50. In these aspects, it is contemplated that a portion of the at least one catalyst can be positioned between each pair of adjacent coolant plates 90.

Optionally, in further exemplary aspects, the plurality of coolant plates 90 can be selectively removable from the housing 20. Thus, in these aspects, it is contemplated that the catalyst bed 50 can be filled with the at least one catalyst and, following positioning of the catalyst within the catalyst bed, the plurality of coolant plates 90 can be at least partially immersed within the catalyst bed.

In one exemplary aspect, the housing 20 can have an outer wall 36, a first inner wall 38, and a second inner wall 40, with the second inner wall being positioned radially inwardly of the first inner wall. In this aspect, it is contemplated that the space between the outer wall 36 and the first inner wall 38 can define the gas feed inlet 22. It is further contemplated that the space between the first inner wall 38 and the second inner wall 40 can define the catalyst bed 50. It is still further contemplated that an inner surface 41 of the second inner wall 40 can define the stripping zone, which generally corresponds to the space within the second inner wall. In exemplary aspects, the first and second inner walls 38, 40 can be circumferential walls that surround the longitudinal axis 28 of the housing 20. In exemplary aspects, the gas inlet 22 can be configured to permit radial flow of gas into the catalyst bed 50. In further exemplary aspects, the plurality of coolant plates 60 can span radially across the catalyst bed 70. In these aspects, it is contemplated that each coolant plate 90 of the plurality of coolant plates can extend radially between the first inner wall 38 and the second inner wall 40. Upon delivery of the gas into the gas inlet 22, the gas travels into the catalyst bed 50, and the plurality of coolant plates 90 can be configured to provide cooling to the catalyst bed during the reaction between the gas and the catalyst within the catalyst bed.

Optionally, in additional exemplary aspects, the catalyst bed 50 can be provided in the form of a plurality of tubes 180. In these aspects, the housing 20 can have an outer wall 36 and an inner wall 40, and the plurality of tubes 180 can be positioned within a space between the outer wall and the inner wall of the housing. In another aspect, it is contemplated that an inner surface 41 of the inner wall 40 can define the stripping zone 70.

Optionally, in another aspect, the reactor 10 can further comprise a cooling jacket 100 that surrounds at least a portion of the product recovery zone 60 to promote separation of lightweight reaction products (e.g., lightweight gaseous products) from wax products. In other optional aspects, the reactor 10 can further comprise a heat exchanger/evaporator 110 positioned within the product recovery zone 60. In these aspects, the heat exchanger/evaporator 110 can optionally comprise a thin-film evaporator.

Optionally, in further aspects, the reactor 10 can further comprise means for separating the wax products based on weight. In one exemplary aspect, the means for separating the wax products can comprise a primary wax product receptacle 120 and a heater 130. In this aspect, the primary wax product receptacle 120 can be positioned in fluid communication with the wax outlet 26 of the housing 20. It is contemplated that the primary wax product receptacle 120 can define an upper wax product outlet 122 and a lower wax product outlet 124. In another aspect, the heater 130 can be configured to heat the wax product receptacle 120 and separate the wax products within the wax receptacle into non-gaseous wax products (e.g., wax and heavies) and gaseous wax products (e.g., non-lightweight gaseous hydrocarbons). In this aspect, the upper wax outlet 122 can be configured to receive the gaseous wax products, and the lower wax outlet 124 can be configured to receive the non-gaseous wax products. Optionally, in additional exemplary aspects, the means for separating the wax products can further comprise first and second secondary wax product receptacles 140, 160 and first and second coolers 150, 170. In these aspects, the first secondary wax product receptacle 140 can be positioned in communication with the upper wax product outlet 122 of the primary wax product receptacle 120, and the second secondary wax product receptacle 160 can be positioned in communication with the lower wax product outlet 124 of the primary wax product receptacle. The first cooler 150 can be configured to cool the first secondary wax product receptacle 140, and the second cooler 170 can be configured to cool the second secondary wax product receptacle 160. Optionally, in exemplary aspects, the means for separating the wax products can further comprise a flash vessel 190 positioned in fluid communication with the wax product outlet 26 of the reactor 10. In these aspects, it is contemplated that the flash vessel 190 can be configured to maintain pressure in the reactor 10. It is further contemplated that the flash vessel 190 can have respective gas and wax product outlets, with the wax product outlet being positioned in fluid communication with the primary wax product receptacle 120.

Methods of Using the Reactor

In use, the disclosed reactors can be used to separate wax reaction products from lightweight gaseous reaction products. In one aspect, a method of separating wax products from non-wax products can comprise performing a chemical reaction using the reactor. In exemplary aspects, the chemical reaction can be an exothermic reaction. In some aspects, the exothermic reaction can be a syngas conversion reaction. Optionally, in these aspects, it is contemplated that the syngas conversion reaction can be a Fischer-Tropsch reaction. In other optional aspects, the chemical reaction can be an endothermic reaction.

In further aspects, the method of separating wax products from lightweight gaseous products can comprise positioning at least one catalyst within the catalyst bed of the reactor as disclosed herein. The method can further comprise selectively delivering at least one coolant to the at least one coolant inlet. The method can further comprise selectively delivering at least one gaseous material to the gas inlet. In exemplary aspects, the method can further comprise collecting at least one reaction product within the product recovery zone. Optionally, in these aspects, the step of collecting at least one reaction product can comprise separating wax reaction products from lightweight gaseous reaction products as disclosed herein. Optionally, the method can further comprise collecting at least one wax reaction product.

In exemplary aspects, the method can further comprise separating the wax reaction products into gaseous wax products and non-gaseous wax products. For example, in these aspects, the wax reaction products can be heated to separate the wax reaction products into non-gaseous wax products (e.g., wax and heavies) and gaseous wax products (e.g., non-lightweight gaseous hydrocarbons) as disclosed herein. Following separation, it is contemplated that the non-gaseous wax products and the gaseous wax products can be cooled as disclosed herein. Optionally, the method can further comprise collecting the non-gaseous wax products (e.g., wax). Optionally, the method can further comprise collecting the gaseous wax products. Optionally, in exemplary aspects, the method can further comprise providing a solvent to at least one of the catalyst bed and the product recovery zone to accelerate wax product separation and/or collection. In these aspects, it is contemplated that the solvent can optionally be configured to produce liquid that can promote movement of the wax reaction products.

For a particular chemical reaction, it is contemplated that any conventional catalyst (along with any conventional promoter or support) for producing a desired reaction product can be used. In exemplary aspects, the at least one catalyst can optionally comprise a Co or Fe-based Fisher Tropsch-catalyst with any promoter or support that is conventionally used to perform a Fischer-Tropsch reaction.

In exemplary aspects, the at least one coolant can comprise one or more of boiler feed water (BFW), steam, or molten salt. However, it is contemplated that the at least one coolant can comprise any material that is conventionally used to provide cooling or heating to a catalyzed reaction, such as, for example and without limitation, a Fischer-Tropsch reaction.

In exemplary aspects, the at least one gaseous material delivered to the gas inlet can comprise a syngas. In these aspects, it is contemplated that the syngas can be formed by contacting a natural gas with steam (and, optionally, carbon dioxide) to produce the syngas using a known reforming process, such as Steam Methane Reforming (SMR), Auto Thermal Reforming (ATR), Partial Oxidation, Adiabatic Pre Reforming (APR), or Gas Heated Reforming (GHR) or any appropriate combination. In further exemplary aspects, the syngas can comprise carbon monoxide, carbon dioxide, or hydrogen, or a combination thereof. In another aspect, the syngas can comprise carbon monoxide and hydrogen. It is contemplated that the feed can contain some impurities, such as, for example and without limitation, sulphur, arsenic, chlorine, hydrogen sulphide, and unwanted reaction products like $CO_2$, methane, hydrocarbons, and the like, which can be recycled as further disclosed herein.

In exemplary aspects, the syngas can be converted into the at least one reaction product by a catalytic process which is usually referred to as the Fischer-Tropsch (FT) process. This is for example described by Van der Laan et al. in Catal. Rev.-Sci. Eng., 41, 1999, p. 255, which is incorporated herein by reference in its entirety. In these aspects, it is contemplated that the at least one reaction product can comprise hydrocarbons. It is further contemplated that the at least one reaction product can comprise at least one olefin, carbon dioxide, and hydrogen. In further exemplary aspects, in addition to the at least one olefin, the at least one reaction product can comprise water, one or more alcohols, or one or more hydrocarbons.

In one aspect, the olefin of the at least one reaction product can comprise C2-C10 hydrocarbons. In another aspect, the olefin can comprise carbons ranging from two carbons to ten carbons, including 3, 4, 5, 6, 7, 8, or 9 carbons. In one aspect, the range of carbon atoms can be derived from any two preceding values. For example, the olefin can comprise carbons ranging from three carbons to nine carbons. In another aspect, the olefin can comprise at least one double bond. In another aspect, the olefin can comprise two double bonds. In a further aspect, the olefin can comprise three double bonds. In still another aspect, the olefin can comprise ethylene, propene, 1-butene, 1-pentene, 1-heptene, 1-hexene, 2-ethyl-hexylene, 2-ethyl-heptene, 1-octene, 1-nonene, or 1-decene, or a combination thereof.

In an additional aspect, the olefin can comprise multiple double bonds. In this aspect, the olefin can be a diolefin. In a further aspect, the olefin can be 1,3-butadiene, 1,4-pentadiene, heptadiene, or a combination thereof. In a further aspect, the olefin can be a cyclic olefin and diolefin. In still another aspect, the olefin can be cyclopentene, cyclopentadiene, cyclohexene, cyclohexadiene, or methyl cyclopentadiene and the like; or a cyclic diolefindiene, e.g., dicyclopentadiene, methylcyclopentadiene dimer and the like.

In further exemplary aspects, the at least one reaction product can comprise one or more paraffins, one or more alcohols, water, or carbon dioxide, or a mixture thereof. In a further aspect, the paraffin can comprise a lightweight paraffin or a heavy paraffin, or a combination thereof. In one aspect, the heavy paraffin can comprise an alkane with more than five carbons. In another aspect, the light paraffin can comprise an alkane with one carbon to five carbons.

Optionally, in various aspects, the disclosed system, apparatus, and methods can be operated or performed on an industrial scale. In one aspect, the system, apparatus, and methods disclosed herein can be configured to produce the disclosed reaction products on an industrial scale. For example, according to further aspects, the system, apparatus, and methods can produce batches of one or more of the disclosed reaction products on an industrial scale.

In various aspects, the disclosed system, apparatus, and methods can be operated or performed on any desired time scale or production schedule that is commercially practicable. As one will appreciate, the processing volume for the reactor can be related to reactor or vessel size, which, optionally, can vary from about 0.1 m$^3$ to about 500 m$^3$. It is contemplated that residence time and/or space velocity can be related to catalyst type and/or performance. Similarly, the handling volume can define the size of the stripping area and the necessary size of wax removal equipment. In another aspect, it is contemplated that the amount of wax produced per unit time can be related to the type and/or performance of catalyst. In exemplary aspects, the amount of wax produced for a particular chemical reaction can range from about 1 wt. % to about 80 wt. %.

In additional aspects, the components of the disclosed system and apparatus can be shaped and sized to permit production of the disclosed reaction products on an industrial scale. Similarly, it is contemplated that the components of the disclosed system and apparatus can comprise materials having material properties that are configured to permit production of the disclosed reaction products on an industrial scale. In further aspects, the components of the disclosed system and apparatus can be shaped and sized to produce the desired reaction products in accordance with the desired time scale or production schedule. Similarly, it is contemplated that the components of the disclosed system and apparatus can comprise materials having material properties that are configured to permit production of the disclosed reaction products in accordance with the desired time scale or production schedule.

In further exemplary aspects, the components of the disclosed system and apparatus can comprise any can comprise any conventional materials that are capable of receiving, housing, and/or contacting reactants, coolants, products, and the like as disclosed herein.

Aspects

Aspect 1: A reactor for separating wax products from lightweight gaseous products of a chemical reaction, the reactor comprising: a housing defining a gas feed inlet, a first gas outlet, and a wax product outlet and having a longitudinal axis, an upper end, and an opposed lower end, the gas feed inlet being positioned proximate the upper end of the housing; a catalyst bed positioned within the housing in fluid communication with the gas feed inlet, the catalyst bed being configured to receive at least one catalyst; a product recovery zone positioned within the housing in fluid communication with the catalyst bed, the product recovery zone being configured to receive at least one reaction product; a stripping zone positioned in fluid communication with the product recovery zone and the first gas outlet, the stripping zone extending upwardly from the product recovery zone relative to the longitudinal axis of the housing, the stripping zone being configured to receive light-weight gas reaction products from the product recovery zone; and a scraper positioned within the product recovery zone, wherein the scraper is configured to separate wax products from interior surfaces of the housing, wherein the first gas outlet is configured to receive lightweight gaseous products from the product recovery zone, and wherein the wax product outlet is configured to receive wax products from the product recovery zone.

Aspect 2: The reactor of aspect 2, further comprising a plurality of coolant plates, the plurality of coolant plates being circumferentially spaced within the catalyst bed, wherein each coolant plate defines at least one channel configured to receive at least one coolant.

Aspect 3: The reactor of aspect 2, wherein the housing defines a coolant inlet, wherein the channels of the plurality of coolant plates are positioned in fluid communication with the coolant inlet.

Aspect 4: The reactor of aspect 3, wherein the housing has an outer wall, a first inner wall, and a second inner wall, wherein the space between the outer wall and the first inner wall defines the gas feed inlet, wherein the space between the first inner wall and the second inner wall defines the catalyst bed, and wherein an inner surface of the second inner wall defines the stripping zone.

Aspect 5: The reactor of aspect 4, wherein the housing defines a coolant outlet, and wherein the channels of the plurality of coolant plates are positioned in fluid communication with the coolant outlet.

Aspect 6: The reactor of aspect 1, further comprising a cooling jacket that surrounds at least a portion of the product recovery zone to promote separation of lightweight reaction products from wax products.

Aspect 7: The reactor of aspect 1, further comprising a heat exchanger/evaporator positioned within the product recovery zone.

Aspect 8: The reactor of aspect 7, wherein the heat exchanger/evaporator comprises a thin-film evaporator.

Aspect 9: The reactor of aspect 1, further comprising means for separating the wax products based on weight.

Aspect 10: The reactor of aspect 9, wherein the means for separating the wax products comprises: a primary wax product receptacle in fluid communication with the wax product outlet, the primary wax product receptacle defining an upper wax product outlet and a lower wax product outlet; and a heater configured to heat the primary wax product receptacle and separate the wax products within the primary wax product receptacle into gaseous wax products and non-gaseous wax products, wherein the upper wax product outlet is configured to receive the gaseous wax products, and wherein the lower wax product outlet is configured to receive the non-gaseous wax products.

Aspect 11: The reactor of aspect 10, wherein the means for separating the wax products further comprises: a first secondary wax product receptacle positioned in communication with the upper wax product outlet of the primary wax product receptacle; a first cooler configured to cool the first secondary wax product receptacle; a second secondary wax product receptacle positioned in communication with the lower wax product outlet of the primary wax product receptacle; and a second cooler configured to cool the second secondary wax product receptacle. Aspect 12: The reactor of aspect 1, wherein the catalyst bed comprises a plurality of tubes positioned in fluid communication with the gas feed inlet and configured to receive the at least one catalyst.

Aspect 13: The reactor of aspect 1, wherein the product recovery zone is positioned below the catalyst bed relative to the longitudinal axis of the housing and configured to receive the at least one reaction product.

Aspect 14: The reactor of aspect 1, wherein the housing further defines a second gas outlet proximate the lower end of the housing and in fluid communication with the product recovery zone, and wherein the second gas outlet is configured to receive non-lightweight gaseous products from the product recovery zone.

Aspect 15: A method of separating wax products from non-wax products, comprising: performing a chemical reaction using the reactor of any one of the preceding aspects.

Aspect 16: The method of aspect 15, wherein the chemical reaction is a syngas conversion reaction.

Aspect 17: A reactor for separating lightweight gaseous products from non-wax products of a chemical reaction, the reactor comprising: a housing defining a gas feed inlet, a first gas outlet, and a wax product outlet and having a longitudinal axis, an upper end, and an opposed lower end, the gas feed inlet being positioned proximate the upper end of the housing; a plurality of tubes positioned in fluid communication with the gas feed inlet and configured to receive at least one catalyst; a plurality of coolant plates circumferentially spaced within the housing, wherein adjacent coolant plates of the plurality of coolant plates cooperate with interior surfaces of the reactor to circumferentially surround at least a portion of at least one tube of the plurality of tubes, wherein each coolant plate defines at least one channel configured to receive at least one coolant; a product recovery zone positioned within the housing in fluid communication with the plurality of tubes, the product recovery zone being configured to receive at least one reaction product; and a stripping zone positioned in fluid communication with the product recovery zone and the first gas outlet, the stripping zone extending upwardly from the product recovery zone relative to the longitudinal axis of the housing, the stripping zone being configured to receive light-weight gaseous products from the product recovery zone, wherein the first gas outlet is configured to receive lightweight gaseous products from the stripping zone, and wherein the wax product outlet is configured to receive wax products from the product recovery zone.

Aspect 18: The reactor of aspect 17, wherein the housing defines a coolant inlet, wherein the coolant inlet is configured to receive at least one coolant to permit circulation of the at least one coolant within the housing.

Aspect 19: The reactor of any one of aspects 17-18, wherein the housing has an outer wall and an inner wall, wherein the plurality of tubes are positioned within a space between the outer wall and the inner wall, and wherein an inner surface of the inner wall defines the stripping zone.

Aspect 20: The reactor of any one of aspects 18-19, wherein the housing defines a coolant outlet, and wherein the coolant outlet is spaced from the coolant inlet relative to the longitudinal axis of the housing.

Aspect 21: The reactor of any one of aspects 17-20, further comprising a cooling jacket that surrounds at least a portion of the product recovery zone to promote separation of lightweight reaction products from wax products.

Aspect 22: The reactor of any one of aspects 17-21, further comprising a heat exchanger/evaporator positioned within the product recovery zone.

Aspect 23: The reactor of aspect 22, wherein the heat exchanger/evaporator comprises a thin-film evaporator.

Aspect 24: The reactor of any one of aspects 17-23, further comprising means for separating the wax products based on weight.

Aspect 25: The reactor of aspect 24, wherein the means for separating the wax products comprises: a primary wax product receptacle in fluid communication with the wax product outlet, the wax product receptacle defining an upper wax product outlet and a lower wax product outlet; and a heater configured to heat the primary wax product receptacle and separate the wax products within the primary wax product receptacle into gaseous wax products and non-gaseous wax products, wherein the upper wax product outlet is configured to receive the gaseous wax products, and wherein the lower wax product outlet is configured to receive the non-gaseous wax products.

Aspect 26: The reactor of aspect 22, wherein the means for separating the wax products further comprises: a first secondary wax product receptacle positioned in communication with the upper wax product outlet of the primary wax product receptacle; a first cooler configured to cool the first secondary wax product receptacle; a second secondary wax product receptacle positioned in communication with the lower wax product outlet of the primary wax product receptacle; and a second cooler configured to cool the second secondary wax product receptacle.

Aspect 27: The reactor of aspect 17, wherein the product recovery zone is positioned below the catalyst bed relative to the longitudinal axis of the housing and configured to receive the at least one reaction product.

Aspect 28: The reactor of claim 1, wherein the housing further defines a second gas outlet proximate the lower end of the housing and in fluid communication with the product recovery zone, and wherein the second gas outlet is configured to receive non-lightweight gaseous products from the product recovery zone.

Aspect 29: A method of separating wax products from non-wax products, comprising: performing a chemical reaction using the reactor of any one of aspects 17-28.

Aspect 30: The method of aspect 29, wherein the chemical reaction is a syngas conversion reaction.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A reactor for separating wax products from lightweight gaseous products of a chemical reaction, the reactor comprising:
   a housing defining a gas feed inlet, a first gas outlet, and a wax product outlet and having a longitudinal axis, an upper end, and an opposed lower end, the gas feed inlet being positioned proximate the upper end of the housing;
   a plurality of tubes positioned in fluid communication with the gas feed inlet and configured to receive at least one catalyst;
   a plurality of coolant plates circumferentially spaced within the housing, wherein adjacent coolant plates of the plurality of coolant plates cooperate with interior surfaces of the reactor to circumferentially surround at least a portion of at least one tube of the plurality of tubes, wherein each coolant plate defines at least one channel configured to receive at least one coolant;
   a product recovery zone positioned within the housing in fluid communication with the plurality of tubes, the product recovery zone being configured to receive at least one reaction product; and
   a stripping zone positioned in fluid communication with the product recovery zone and the first gas outlet, the stripping zone extending upwardly from the product recovery zone relative to the longitudinal axis of the housing, the stripping zone being configured to receive light-weight gaseous products from the product recovery zone,
   wherein the first gas outlet is configured to receive lightweight gaseous products from the stripping zone, and wherein the wax product outlet is configured to receive wax products from the product recovery zone.

2. The reactor of claim 1, wherein the housing defines a coolant inlet, wherein the coolant inlet is configured to receive at least one coolant to permit circulation of the at least one coolant within the housing.

3. The reactor of claim 1, wherein the housing has an outer wall and an inner wall, wherein the plurality of tubes are positioned within a space between the outer wall and the inner wall, and wherein an inner surface of the inner wall defines the stripping zone.

4. The reactor of claim 2, wherein the housing defines a coolant outlet, and wherein the coolant outlet is spaced from the coolant inlet relative to the longitudinal axis of the housing.

5. The reactor of claim 1, further comprising a cooling jacket that surrounds at least a portion of the product recovery zone to promote separation of lightweight reaction products from wax products.

6. The reactor of claim 1, further comprising a heat exchanger/evaporator positioned within the product recovery zone.

7. The reactor of claim 6, wherein the heat exchanger/evaporator comprises a thin-film evaporator.

8. The reactor of claim 1, further comprising means for separating the wax products based on weight.

9. The reactor of claim 8, wherein the means for separating the wax products comprises:
- a primary wax product receptacle in fluid communication with the wax product outlet, the primary wax product receptacle defining an upper wax product outlet and a lower wax product outlet; and
- a heater configured to heat the primary wax product receptacle and separate the wax products within the primary wax product receptacle into gaseous wax products and non-gaseous wax products,
- wherein the upper wax product outlet is configured to receive the gaseous wax products, and wherein the lower wax product outlet is configured to receive the non-gaseous wax products.

10. The reactor of claim 9, wherein the means for separating the wax products further comprises:
- a first secondary wax product receptacle positioned in communication with the upper wax product outlet of the primary wax product receptacle;
- a first cooler configured to cool the first secondary wax product receptacle;
- a second secondary wax product receptacle positioned in communication with the lower wax product outlet of the primary wax product receptacle; and
- a second cooler configured to cool the second secondary wax product receptacle.

11. The reactor of claim 1, wherein the product recovery zone is positioned below the catalyst bed relative to the longitudinal axis of the housing and configured to receive the at least one reaction product.

12. The reactor of claim 1, wherein the housing further defines a second gas outlet proximate the lower end of the housing and in fluid communication with the product recovery zone, and wherein the second gas outlet is configured to receive non-lightweight gaseous products from the product recovery zone.

13. A method of separating wax products from non-wax products, comprising:
performing a chemical reaction using a reactor, the reactor comprising:
- a housing defining a gas feed inlet, a first gas outlet, and a wax product outlet and having a longitudinal axis, an upper end, and an opposed lower end, the gas feed inlet being positioned proximate the upper end of the housing;
- a plurality of tubes positioned in fluid communication with the gas feed inlet;
- a plurality of coolant plates circumferentially spaced within the housing, wherein adjacent coolant plates of the plurality of coolant plates cooperate with interior surfaces of the reactor to circumferentially surround at least a portion of at least one tube of the plurality of tubes, wherein each coolant plate defines at least one channel;
- a product recovery zone positioned within the housing in fluid communication with the plurality of tubes; and
- a stripping zone positioned in fluid communication with the product recovery zone and the first gas outlet, the stripping zone extending upwardly from the product recovery zone relative to the longitudinal axis of the housing;
receiving at least one catalyst within at least one tube of the plurality of tubes;
receiving at least one coolant within the at least one channel of at least one coolant plate of the plurality of coolant plates;
receiving at least one reaction product within the product recovery zone;
receiving lightweight gaseous products from product recovery zone within the stripping zone;
receiving lightweight gaseous products from the stripping zone within the first gas outlet; and
receiving wax products from the product recovery zone within the wax product outlet.

14. The method of claim 13, wherein the chemical reaction is a syngas conversion reaction.

15. The reactor of claim 1, further comprising a scraper positioned within the product recovery zone, wherein the scraper is configured to separate wax products from interior surfaces of the housing.

16. The method of claim 13, further comprising separating the wax products based on weight.

17. The method of claim 16, wherein separating the wax products comprises:
receiving the wax products within a primary wax product receptacle in fluid communication with the wax product outlet, the primary wax product receptacle defining an upper wax product outlet and a lower wax product outlet;
heating the primary wax product receptacle to separate the wax products within the primary wax product receptacle into gaseous wax products and non-gaseous wax products;
receiving the gaseous wax products within the upper wax product outlet; and
receiving the non-gaseous wax products within the lower wax product outlet.

18. The method of claim 17, wherein separating the wax products further comprises:
positioning a first secondary wax product receptacle in communication with the upper wax product outlet of the primary wax product receptacle;
cooling the first secondary wax product receptacle;
positioning a second secondary wax product receptacle in communication with the lower wax product outlet of the primary wax product receptacle; and
cooling the second secondary wax product receptacle.

19. The method of claim 13, wherein the product recovery zone is positioned below the catalyst bed relative to the longitudinal axis of the housing.

20. The method of claim 13, wherein the reactor further comprises a scraper positioned within the product recovery zone, and wherein the method further comprises using the scraper to separate wax products from interior surfaces of the housing.

* * * * *